United States Patent [19]

Buckley et al.

[11] Patent Number: 4,806,465

[45] Date of Patent: Feb. 21, 1989

[54] CYTOPLASMIC ANTIGENS OF CANDIDA ALBICANS AND METHODS OF USING THE SAME

[75] Inventors: Helen R. Buckley; Michael T. Largen, both of Philadelphia, Pa.; Nancy A. Strockbine, Bethesda, Md.

[73] Assignee: Temple University of the Commonwealth System of Higher Education, Philadelphia, Pa.

[21] Appl. No.: 32,111

[22] Filed: Mar. 30, 1987

Related U.S. Application Data

[60] Division of Ser. No. 571,129, Jan. 16, 1984, Pat. No. 4,670,382, which is a continuation-in-part of Ser. No. 557,296, Dec. 3, 1983, abandoned.

[51] Int. Cl.⁴ .................. G01N 53/00; A61K 45/00; A61K 35/72; C07K 15/04
[52] U.S. Cl. .......................................... 435/7; 435/68; 435/240.27; 436/548; 436/518; 530/371; 424/88; 424/85.8
[58] Field of Search .................. 435/68, 172.2, 240.27, 435/7, 948; 436/548; 424/85, 88; 530/387, 37

[56] References Cited

U.S. PATENT DOCUMENTS

| 4,051,232 | 4/1977 | Protzman et al. | 436/515 |
| 4,490,290 | 8/1984 | Gani et al. | 435/948 |
| 4,670,382 | 6/1987 | Buckley et al. | 435/948 |

OTHER PUBLICATIONS

Guinet et al, "Etudes Antigeniques de Candida Albicans Serotypes A et B Antigens Solubles Specifiques du Serotype A", *Bulletin de al Sociaete Francaise de Mycologie Medicale* 9(1) pp. 91–96 (1980).

Jones, J. M., "Quantitation of Antibody Against Cell Wall Mannan and a Major Cytoplasmic Antigen of Candida in Rabbits, Mice and Humans", *Infection and Immunity*, 30: 78–89 (1980).

Greenfield, R. A. and Jones, J. M., "Purification and Characterization of a Major Cytoplasmic Antigen of Candida Albicans", *Infection and Immunity*, 34: 469–477 (1981).

Hopfer et al, "Detection by Counterimmunoelectrophoresis of Anti-Candida Precipitins in Sera from Cancer Patients", *American Journal of Clinical Pathology* 72(2) pp. 215–218 (1979).

Ruchel, "Properties of a Purified Protease from the Yeast Candida Albicans", *Biochimica et Biophysica Acta* 659 pp. 99–113 (1981).

MacDonald et al, "Inducible Protease of Candida Albicans in Diagnostic Serology and the Pathogenesis of Systemic Candidosis", *Journal of Medical Microbiology* 13(3) pp. 423–435 (1980).

Fukazawa et al, "Response and Specificity of Antibodies for Candida Albicans", *Journal of Bacteriology* 95(3) pp. 754–763 (1968).

Sevier et al, "Monoclonal Antibodies in Clinical Immunology", *Clinical Chemistry* 27 (11) pp. 1797–1806 (1981).

Kwan et al, "Production of Monoclonal Antibodies", *Genetic Engineering*, 2, pp. 31–46 (1980).

*Primary Examiner*—John E. Tarcza
*Attorney, Agent, or Firm*—Seidel, Gonda, Lavorgna & Monaco

[57] ABSTRACT

Two novel hybridoma cell lines, ATCC #HB-8397 and ATCC #HB-8398 produce monoclonal antibody monospecific to a single determinant shared by a set of three closely related cytoplasmic antigens of *Candida albicans*. The antigens have molecular weights of 120–135 Kd, 48–52 Kd, and 35–38 Kd. The hybridomas are formed by fusing splenocytes from immunized BALB/c mice with SP2/O-Ag 14 myeloma cells. Monoclonal and monospecific, polyclonal antibodies to these cytoplasmic antigens find application in the immunodiagnosis of Candida infections.

A procedure is provided for preparing partially purified cytoplasmic antigen of pathogenic Candida species for administration to splenocyte-donating mice. Also provided is a method for the biochemical purification of cytoplasmic antigen of a pathogenic Candida species used for the preparation of monoclonal and monospecific, polyclonal antisera thereto.

7 Claims, 4 Drawing Sheets

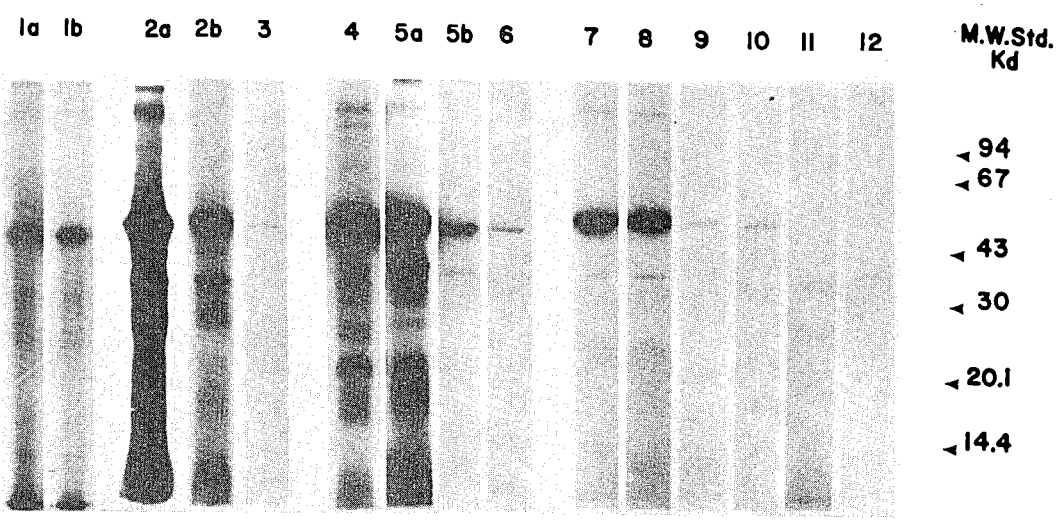
FIG. 2
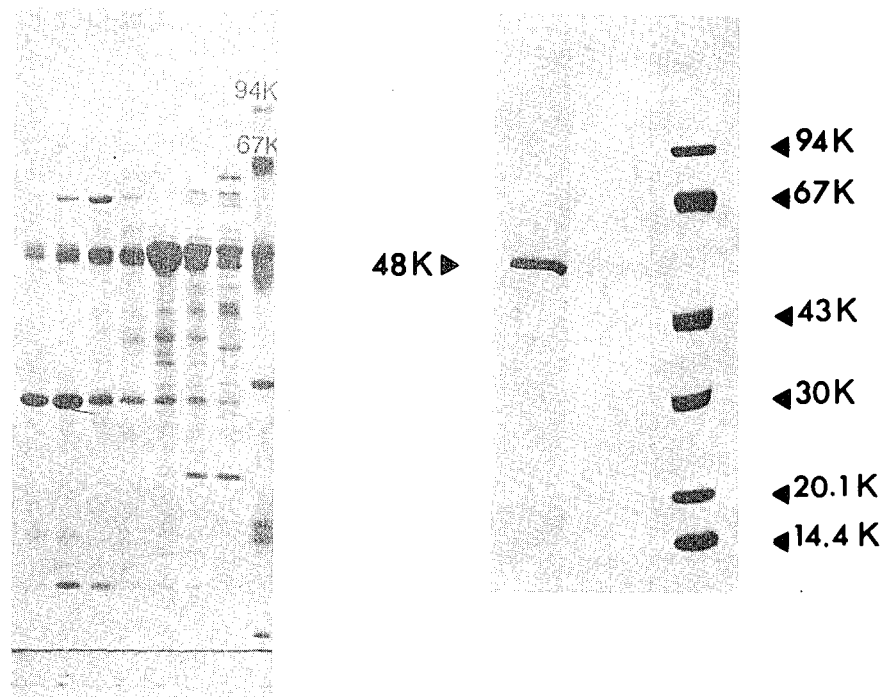
FIG. 1
FIG. 5

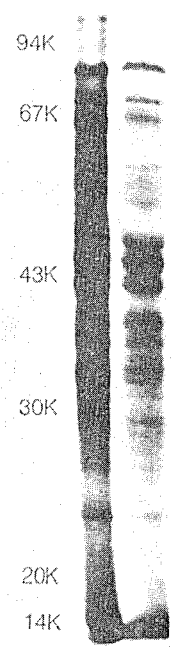
FIG. 6
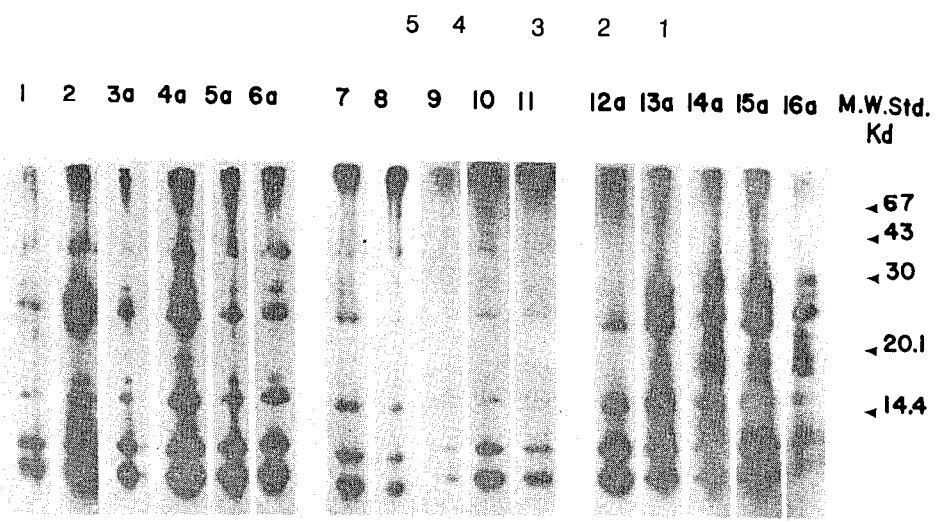
FIG. 7
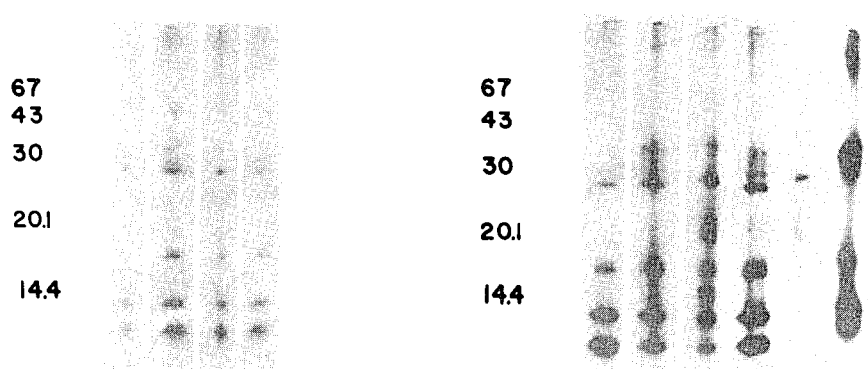

CYTOPLASMIC ANTIGENS OF CANDIDA ALBICANS AND METHODS OF USING THE SAME

REFERENCE TO GOVERNMENT GRANT

The invention discribed herein was supported by National Institutes of Health Grants Al 07141 and Al 14695. The United States government has a certain rights in the invention.

This is a divisional of co-pending application Ser. No. 571,129, filed on Jan. 16, 1984, now U.S. Pat. No. 4,670,382, which is a continuation-in-part of application Ser. No. 557,296, filed on Dec. 3, 1983, now abandoned.

FIELD OF THE INVENTION

This invention relates to hybrid cell lines for production of monoclonal antibodies to a set of cytoplasmic antigens of the fungus Candida albicans, to the antibody so produced, and to diagnostic and therapeutic methods using this antibody. This invention also relates to the purification of one component of the set of cytoplasmic antigens, production of monospecific polyclonal antibody against this antigen, and to diagnostic and therapeutic methods using this antibody.

DESCRIPTION OF THE PRIOR ART

In 1975 Kohler and Milstein (Nature 256:495–497) described the fusion of myeloma cells and immune spleen cells from mice. These hybrid cell lines, or hybridomas, had characteristics that neither the parental myeloma cells nor the immune spleen cells possessed; these hybrid cells were capable of continuously producing homogeneous (monoclonal) antibodies. Before this time only polyclonal sera could be obtained. In order to obtain antibodies which were reactive with only a single antigen, laborious purification techniques were required to provide highly purified antigen for immunization. Even if successful, these methods did not provide antibodies which were as homogeneous and well defined as the monoclonal antibodies produced from hybridoma cell lines. A review article by Milstein in *Scientific American* (243:66–74, 1980) summarizes the advantages of monoclonal antibodies as compared to the conventional polyclonal monospecific antisera raised in rabbits, goats, and other experimental animals. There are now hundreds of references in the scientific literature to the production of monoclonal antibodies against a variety of antigens. Several books contain a series of papers on the production and uses of monoclonal antibodies (e.g. *Current Topics In Microbiology And Immunology*, Vol. 81, "Lymphocyte Hybridomas," F. Melchers, M. Potter, and N. Warner, eds., Springer-Verlag, 1978; and *Monoclonal Antibodies, Hybridomas: A New Dimension In Biological Analysis*, R. Kennett,.T.J. McKearn, and K.B. n=chtol, eds., Plenum Press, 1980).

Although the conceptual basis of hybridoma production is now reasonably well understood, the production of monoclonal antibodies for any given antigen is still an empirical process. When attempting to make antibodies against complex mixtures of antigens, such as those of a microorganism, the outcome becomes even more uncertain. In the case of *C. albicans,* Axelsen has estimated that there are more than 78 different potential antigenic species which can be recognized (Infect. Immun. 7:949–960, 1973). For this reason the choice of an immunogen is critical in producing antibody potentially useful for diagnostic and therapeutic purposes.

There have been no previous reports of monoclonal antibody production against cytoplasmic antigens of the fungus *C. albicns.* In fact, very little has been done in terms of the characterization of Candida antigens which are recognized by antibodies in the sera of patients with invasive candidiasis. Work from our laboratory (Glew et al., Am.J.Med. 84:586–591, 1978) established that anti-cell wall mannan antibodies were probably not important diagnostic indicators, since most individuals irrespective of current or prior infection with *C. albicans* possess anti-mannan antibodies in their serum. Subsequent studies indicated that.cytoplasmic antigens were probably more important in diagnosing an ongoing Candida infection (Syverson, R.E., and Buckley, H.R., J. Clin.Path. 68:29–38, 1978). Recent studies (Strockbine, Largen, Zweibel, and Buckley, accepted, *Inf. & Imm.*) have identified several antigens which are recognized by antibodies in the serum of patients with disseminated candidiasis. The antibody levels against a 48–52 kilodalton (Kd) antigen were quantified in the sera of patients with invasive candidiasis, patients with noninvasive, superficial candidiasis, patients with other fungal infections and normal healthy individuals. The results of this study showed that patients with invasive candidiasis had significantly higher levels of antibodies against the 48–52 Kd protein than did the control groups at $p<0.001$, a highly significant difference.

Disseminated candidiasis is a serious clinical problem in immunosuppressed patients and in individuals with indwelling venous catheters (Myerowitz, R., et al., J.Clin.Path. 68:29–38, 1977). Although Candida can often be cultured from colonized sites, blood cultures are frequently negative. The therapeutic course involves administration of drugs such as Amphotericin B which, although effective against the pathogen, often result in severe kidney damage. It is thus imperative for the clinician to ascertain whether dissemination of Candida has occurred. Immunological methods can be used to aid in the diagnosis of other fungal diseases such as cryptococcosis, aspergillosis, histoplasmosis, and coccidioidomycosis (*Manual of Clinical Microbiology*, E.H. Lennette, A. Ballows, W. J. Hausler, and J. Truant, eds., American Society for Microbiology, 1980). Immunological methods are very important in diagnostic tests, because of their specificity and, as noted above, monoclonal antibodies are even more specific.

The identification and characterization of an antigen with which antibodies of patients with candidiasis react makes it possible to design an immunological test, such as an enzyme-linked immunosorbent assay (ELISA), radioimmunoassay (RIA), or latex agglutination to test whether or not an individual has antibodies specific for that antigen. A positive reaction would indicate an ongoing Candida infection and would indicate drug therapy. As noted above, however, disseminated candidiasis often occurs in patients who are immunosuppressed either because of disease or as part of ongoing therapy, as in the case of cancer patients undergoing chemotherapy. Thus, detection of antibodies to Candida is impractical. An additional problem with an antibody detection system for Candida is the lag time required for an immune response in the host.

According to the present invention, immunological methods can be used to detect antigen (rather than antibody) which may be present in body fluids, including serum, urine, spinal fluid, or in mucus secretions. Antigen detection methods require specific antibody to antigens which are present in these fluid,s at detectable levels. The antigens described herein are good candidates for detection. Immunocompetent individuals with disseminated candidiasis have mounted an immune response against these antigens, indicating that these proteins are available to the immune system in sufficient concentration to trigger an immune response.

At the present time, although various tests have been described in the scientific literature for both antibody detection and antigen detection for the diagnosis of disseminated candidiasis, none of these tests employing existing antibodies has the requisite reliability and predictive value positive to make it clinically useful. In none of these tests are the relevant antigens described in detail.

SUMMARY OF THE INVENTION

According to the present invention, two novel hybridomas have been discovered providing cell lines which are capable of producing novel monoclonal antibodies of class $I_gG$ against a set of closely related cytoplasmic antigens of molecular weights 120–135 kilodaltons (Kd), 48–52 Kd, and 35–38 Kd as determined by sodium dodecyl sulfate-polyacrylamide gel electrophoresis. The hybridomas comprise a fused cell hybrid of a BALB/c mouse spleen cell fused to a mouse myeloma. The donor mouse is previously immunized with cytoplasmic antigens of *C. albicans*. The hybridomas are, respectively, ATCC #HB-8397 and ATCC #HB-8398. The antibodies so produced are monospecific for a single determinant shared by the closely related cytoplasmic antigens These monoclonal antibodies are not contaminated with other immunoglobulins directed against any other Candida antigens.

There has also been discovered according to this invention a procedure for the production of a biochemically pure preparation of one of the protein antigens (48–52 Kd) recognized by the monoclonal antibodies. This pure preparation is used to prepare monospecific polyclonal anti-sera which recognize the same three antigens as the monoclonal antibodies. The resulting monospecific polyclonal antisera can be used alone or in conjunction with the monoclonal antibodies. Both the monoclonal as well as the polyclonal monospecific sera allow the detection of a specific antigen of *C. albicans* which appears to be important in the diagnosis of disseminated candidiasis.

The hybridoma cell lines according to the present invention provide a novel source of homogeneous, reproducible reagents (monoclonal antibodies) for the detection of a specific *C. albicans* antigen. The biochemical purification of this antigen, together with the production of polyclonal monospecific antisera thereto, provide a source of antigen and an alternative source of antibodies which were not possible using the prior art.

The hybridoma cell lines of the present invention are prepared by immunizing mice with cytoplasmic extract of *C. albicans*, removing the spleen cells and making a suspension thereof. The spleen cells are fused with mouse myleoma cells in the presence of a fusion promotor. The fused cells are diluted and cultured in separate wells in a medium which will not support the unfused myeloma or spleen cells. The supernatant in each well is evaluated for the presence of antibody to cytoplasmic antigens of *C. albicans*. Hybridomas producing antibody reacting with *C. albicans* cytoplasmic antigens 35–38 Kd, 48–52 Kd or 120–135 Kd are selected and cloned. The antibody is recovered from the supernatant of the clone.

Alternatively, the clones are transferred intraperitoneally into mice, and the resulting malignant ascites or serum containing the desired antibody is harvested.

A process for preparing polyclonal, monospecific antibodies against 35–38 Kd, 48–52 Kd, or 120–135 Kd cytoplasmic antigen of *C. albicans* is provided. An animal is immunized with a biochemically pure preparation of one of these antigens, and the polyclonal antibody is harvested from the serum of the animal.

A process for preparing partially purified cytoplasmic antigen of a pathogenic Candida species for the preparation of monoclonal antibodies thereto is provided. A cytoplasmic extract of mycelia or yeast of the fungus is fractionated by affinity chromatography to remove cell wall mannan, glucan and manno-/glucoprotein complexes. The mannan-depleted extract is further fractionated by ion exchange chromotography. A fraction of the eluent is selected for immunizing an animal donor whose spleen cells are used for hybridoma production.

Also provided is a process for preparing biochmically pure cytoplasmic antigen of a pathogenic Candida species for the preparation of either monoclonal or monospecific polyclonal antibodies thereto. The mannan-depleted cytoplasmic extract of mycelia or yeast is fractionated by ion exchange chromatography as before. A fraction of the eluent is selected. The component protein species thereof are separated by gel electrophesis. A band of molecular weight containing the desired antigenic species in substantially pure form is selected.

It is, accordingly, one object of this invention to provide hybridomas which produce antibodies against a set of three closely related cytoplasmic antigens of *C. albicans* which are important in immunodiagnostics of Candida infections. fections.

It is a further aspect of the present invention to provide methods for the partial purification of the immunogen and methods using this immunogen to prepare these hybridoms.

A further object of this invention is to provide essentially homogeneous antibody against this set of cytoplasmic antigens of *C. albicans*.

It is an object of this invention to provide methods for the preparation of partially purified cytoplasmic antigen of a pathogenic Candida species for the preparation of monoclonal antibodies thereto.

Another object of this invention is to provide methods for the biochemical purification of a cytoplasmic antigen of a pathogenic Candida species such that this purified protein can be used for the preparation of monospecific polyclonal antisera thereto.

Another object of this invention is to provide methods for the biochemical purification of a cytoplasmic antigen of a pathogenic Candida species such that this purified protein can be used for the preparation of monospecific polyclonal antisera thereto.

A still further object of this invention is to provide methods for diagnosis or treatment of disease using monoclonal and polyclonal, monospecific antibodies directed against defined cytoplasmic antigens of *C. albicans*.

Other objects and advantages of the invention will become apparent from the examination of the present disclosure.

Hybridomas were prepared generally following the method of Kohler and Milstein (Nature 256:495–497). Following immunization of mice with a partially purified, mannan-free preparation of *C. albicans* cytoplasmic antigens, the immunized spleen cells were fused with a mouse myeloma cell line and the resultant hybridomas were screened for antibodies reactive with the partially pure antigen preparation used for immunization. In order to identify those hybridomas producing antibodies against an antigen which we had previously found to be recognized exclusively by antibodies from patients with disseminated candidiasis (Strockbine, Largen, Zweibel, and Buckley, accepted, *Inf. & Imm.*), positive hybridomas were screened by immunoprecipitation. Two hybridomas producing antibodies against this antigen were subsequently cloned and characterized. In addition, it was found that these monoclonal antibodies recognize a determinant shared by two other closely related cytoplasmic antigens. Thus, then, two hybridoma lines were isolated which recognize a set of three closely related cytoplasmic antigens of *C. albicans*.

The identification of the immunologically important antigen prior to attempts to raise monoclonal antibodies was an important factor in the success of these procedures. Nonetheless, it cannot be assumed, especially with a partially purified immunogen, that it will be possible to raise the desired antibodies. In addition, monoclonal antibodies, although possessing all the advantages described above, sometimes have limitations that polyclonal antibodies do not. Because of this, methods were derived which allow the preparation of apparently biochemically pure antigen for use as an immunogen in the preparation of polyclonal monospecific antisera. No prior method existed for the complete sequence of purification steps which are required for the purification of this immunogen. This homogeneous immunogen has been used for the production of monospecific polyclonal antibodies. It can also be an effective immunogen for the production of monoclonal antibodies.

DETAILED DESCRIPTION OF THE INVENTION

Figure 3:
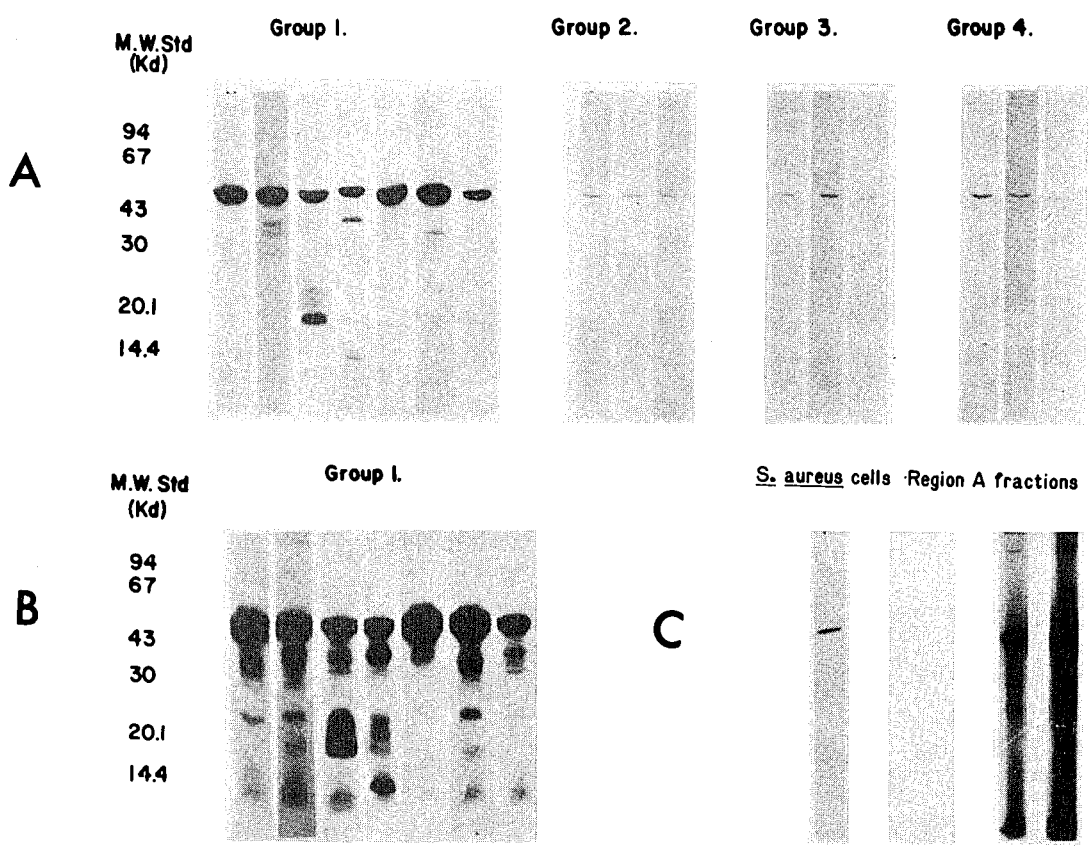

The method of preparing the hybridomas of the present invention generally comprises the following steps:

A. Immunizing mice with a partially purified antigen prepared from *Candida albicans*

BALB/c mice were immunized width an antigen purified from the cytoplasmic extract of *C. albicans*. The antigen was prepared by mechanical disruption of the mycelial-phase cells from *C. albicans*. The resulting cytoplasmic extract was subsequently centrifuged to remove cell walls, membranes, and intracellular organelles and then fractionated by affinity and ion exchange chromatography. A detailed description of the antigen purification protocol is presented in Example 1, section A. It is likely that the cytoplasmic extract from yeast-phase cells of *C. albicans* as well as other Candida species could be used for antigen production. It is also conceivable.that other cell disruption and fractionation techniques could be employed to produce this antigen. While it has been found that BALB/c mice produced suitable quantities of immune splenocytes for hybridoma production, it is contemplated that other mouse strains could be employed. The immunization schedule and antigen concentrations should be such as to produce useful quantities of suitably primed splenocytes. The following immunization schedule was found to be effective.

Four inoculations with 37–50 μg of protein on days 0, 43, 157, and 247 were administered as follows: subcutaneously in incomplete Freund's adjuvant on days 0 and 157; IItraperitoneally in alum on day 43; and intraperitoneally in saline on day 247. Four days after the final immunization the mice were sacrificed for hybridoma production.

B. Aseptically removing the spleens from the immunized mice and making a spleen suspension in an appropriate medium About 3 ml of medium per spleen is sufficient. These experimental techniques are well known and have been published in journals and books on basic laboratory procedures in immunology.

C. Fusing the spleen cells with mouse myeloma cells from a suitable cell line by the use of a suitable fusion promotor The preferred fusion promotor is polyethylene glycol 1000 (average molecular weight 1000–4000, commercially available as PEG 1000); however, other fusion promotors could be employed. The preferred fusion technique is performed with the myeloma and spleen cells in an adherent monolayer; however, other fusion techniques known in the art (e.g., suspension or pellet fusion techniques) may be used. The optimal cell ratio is about two to three spleen cells per myeloma cell; however, this ratio may be larger or smaller, depending on the source of spleen or myeloma cells. Many mouse myeloma cell lines are known and available, generally from members of the academic community or various deposit banks, such as the American Type Culture Collection, Rockville, Md. The cell line used should preferably be of the so-called "drug-resistant" type. This is desirable so that unfused myeloma cells will not survive in a selective medium, while hybrids will survive. The most common class is 8-azaguanine-resistant cell lines, which lack the enzyme hypoxanthine guanine phosphoribosyl transferase and hence will not be supported by HAT (hypoxanthine, aminopterin and thymidine) medium. It also generally preferred that the myeloma cell line used be of the so-called "non-secreting" type (e.g., the myeloma cell itself does not produce any antibody), although secreting types may be used. In certain cases, however, secreting myeloma lines may be preferred.

D. Diluting and culturing the mixture of unfused spleen cells, unfused myeloma cells and fused cells in a selective medium in separate containers The selective medium will not support the drug-resistant (e.g., 8-azaguanine-resistant) unfused myeloma cells. The selective medium is employed after the fusion for a sufficient time (about 7–10 days) to allow death of the unfused myeloma cells. Since the unfused myeloma cells are non-malignant, they have only a finite number of generations, and after 7–10 days they will fail to reproduce and eventually will die. The fused cells, on the other hand, continue to reproduce, because they possess the malignant quality of the myeloma parent and the ability of the spleen cell parent to survive in the selective medium. Thus, after the fusion, the cells are resuspended in the selective medium (e.g., HAT medium) and added to separate containers (e.g., each well of a 96-well microtiter plate). The cells may be resuspended with a volume of diluent which is statistically calculated to isolate a certain number of cells (e.g., 1–4 cells per well) in each separate container (e.g., each well of a microtiter plate).

E. Evaluating the supernatant in each container (well) containing a hybridoma for the presence of antibody to the Candida proteins The screening assay used was an enzyme-linked immunosorbent assay (ELISA); however, other screening assays (e.g., RIA) could be employed.

F. Selecting and cloning (e.g., by limiting dilution or soft agar) hybridomas producing the desired antibody Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant. The suitable medium and suitable length of culturing time are known or are readily determined. This in vitro technique produces essentially monospecific monoclonal antibody, essentially free from other anti-Candida immune globulin. There is a small amount of other immune globulin present, since the medium contains xenogeneic serum (e.g., fetal calf serum). One drawback to this in vitro method is that it may not produce a sufficient quantity or concentration of antibody for some purposes, since the concentration of monoclonal antibody is only about 50 $\mu$g/ml.

To produce a much greater concentration of slightly less pure monoclonal antibody, the desired hybridoma may be injected into mice, preferably syngeneic or semi-syngeneic mice. The hybridoma will cause formation of antibody-producing tumors after a suitable incubation time, which will result in a high concentration of the desired antibody (about 5–20 mg/ml) in the bloodstream and peritoneal exudates (ascites) of the host mouse. Although these host mice also have normal antibodies in their blood and ascites, the concentration of these normal antibodies is only about 5% of the total antibody concentration in these fluids. Moreover, since these normal antibodies are not anti-Candida in their specificity, the monoclonal antibody obtained from the harvested ascites or from the serum is essentially free of any contaminating anti-Candida immune globulin. This monoclonal antibody is high titer (active at dilutions of 1:30,000 or higher). Where the myeloma cell line used for hybridoma production is a "non-secreting" line, all the antibody produced should be reactive against its antigen(s). For hybridomas produced from a "secreting" myeloma parent, the antibody secreted by these hybrid cells may incorporate the light chain produced by the myeloma cell instead of the light chain produced by the spleen cell. Antibodies with the myeloma light chain are non-specific, "nonsense" antibodies which merely dilute the functionally active monoclonal antibody without detracting from the antibody's specificity. If a secreting myeloma line is used, the ascites and serum will still contain a high ratio of specific to non-specific immune globulin.

EXAMPLE I

Production of Monoclonal Antibodies A2C7 and C2C7

A. Antigen Preparation

Candida albicans, serotype A (Hasenclever B311, NIH), was grown on Sabouraud's slants for 18–24 hours at 25° C. The growth from one slant was inoculated into several flasks containing 50 ml of a liquid synthetic medium (Lee et al., Sabouraudia 13:148–153, 1975) and incubated at 25° on a gyrotory shaker at 150 rpm for 18 hours. Aliquots (approximately 1 ml) of the growth from these flasks were added to new flasks containing 100 ml of the above liquid medium and rotated at 150 rpm for 24 hours at 37° C. The cells were harvested by centrifugation and resuspended with buffer (0.05 M Tris-HCl, pH 7.4, with 0.02%[w/v]NaN$_3$). Cells grown under these conditions were 90% mycelium and 10% yeast cells.

The cell slurry was disrupted mechanically in a Braun homogenizer for 8 minutes, using a 1:1 mixture of glass beads to cell slurry. Unbroken cells and cellular debris were removed by centrifugation at 10,000$\times$g at 4° C. for 30 minutes. The supernatant was collected and the pellet was washed three times in buffer (0.01 M sodium phosphate buffer, pH 7.4) by centrifugation as described above. The original and wash supernatants were pooled and centrifuged at 80,000$\times$g for 90 minutes at 4° C. The supernatant was collected, using a syringe to avoid the lipid layer at the surface of the tube, and dialyzed against dilute buffer (0.001 M Tris-HCl, pH 7.4, containing 0.02% [w/v]NaN$_3$). The protein content was determined by the method of Lowry et al. (J.Biol.Chem. 193:265–275, 1951). The material that remained in solution after the high-speed centrifugation was designated as the mycelial-phase cytoplasmic extract (MCE).

The MCE was subsequently fractionated by affinity chromatography. The MCE (42–114 mg protein) was passed over a concanavalin A affinity column to remove cell wall mannan, glucan, and manno-/glucoprotein complexes. A Con A-Sepharose 4B (Pharmacia, Uppsala, Sweden) column (50-ml bed volume) is preferred. A loading buffer of pH between about 6.5 and about 7.5 is used, containing 0.001 M to 0.01 M concentrations of the following cations: $Mn^{2+}$, $Mg^{2+}$ and $Ca^{2+}$. The preferred loading buffer is 0.05 M Tris-HCl, pH 7.4, with 0.001 M MgCl$_2$, 0.001 M MnCl$_2$, and 0.001 M CaCl$_2$ (buffer A). NaN$_3$ may be present as a preservative. The unbound, mannan-depleted material (MD-MCE) was pooled, dialyzed against a lyophilizable buffer of pH 7–8, and lyophilized. The preferred lyophilizable buffer is 0.001 M ammonium bicarbonate buffer, pH 7.4. Approximately 60% of the material loaded on the column was recovered in the unbound fractions.

The MD-MCE was fractionated further by DEAE ion exchange chromatography. The MD-MCE proteins (80.7 mg) were dissolved in running buffer, 0.05 M Tris-HCl, pH 7.8, and applied to a DEAE ion exchange column. A DEAE-Sephacel (Pharmacia) column (70-ml bed volume) is preferred. Other suitable cationic running buffers include ammonium, imidazole, etc. The proteins were eluted with a linear salt gradient from 0 to 0.22 M chloride ion in the running buffer. NaCl is preferred as a source of chloride ion. The fractions eluting at 0.028 to 0.066 M NaCl were pooled, dialyzed against 0.001 M Tris-HCl, pH 7.4, and assayed for protein. Proteins from these fractions were used to immunize the mice for hybridoma production. FIG. 1 shows the fractions eluted from the DEAE ion exchange column at 0.02–0.06 M NaCl as analyzed by sodium dodecyl sulfate-polyacrylamide gel electrophoresis and stained with the silver technique.

B. Immunization and Somatic Cell Hybridization

Female BALB/c mice (Fox Chase Institute for Cancer Research, Philadelphia, PA) were immunized subcutaneously with 50 μg of protein in incomplete Freund's adjuvant on day 0 and intraperitoneally with 50 μg of protein in alum on day 43. On day 157, the mice were inoculated subcutaneously with 37 μg of protein in incomplete Fruendμs adjuvant and on day 247 the mice received 50 μg of protein intraperitoneally in saline. Four days after the last immunization (day 251), the mice were sacrificed by cervical dislocation and the spleens were aseptically removed for the fusion. A single cell suspension in Hanks' balanced salt solution (GIBCO, Grand Island, N.Y.) was made by The red blood cells were removed by lysis with 0.17 M ammonium chloride for 10 minutes on ice. The unlysed splenocytes and the SP2/0-Ag 14 myeloma cells (Schulman, Nature 276:269–270) were washed extensively (three times) in serum-free medium to remove serum proteins which interfere with the fusion process.

Cell fusion with SP2/0-Ag 14 myeloma cells and mouse splenocytes was performed according to a modified procedure from McKearn (In *Monoclonal Antibodies, Hybridomas: A New Dimension In Biological Analysis*, R. H. Kennett, T. J. McKearn, and K.B. Bechtol, eds., Plenum Press, pp. 368–369, 1980) and Gopalakrishnan (J.Cell Biol. 83:448a, 1979). The cells were fused by a 30- to 45-second exposure to a solution of 50% (v/v) polyethylene glycol 1000 (J.T. Baker Chemical, Phillipsburg, N.J.) and 50% (v/v) Dulbecco's Modified Eagle's Medium (DMEM; GIBCO) in an adherent monolayer on a Con A-coated tissue culture dish (No. 3060, Costar, Cambridge, Mass.). Cells were mixed at a ratio of 2 to 3 splenocytes to 1 myeloma cell, and $7-10\times10^7$ total cells were added to each fusion dish. The fusion dishes were prepared by incubating tissue culture dishes with 1 ml of 0.1 M sodium acetate, pH 4.8, containing 15 mg/ml Con A (Calbiochem-Behring, LaJolla, Calif.), and 1 ml of 0.1 M sodium acetate, pH 4.8, containing 50 mg/ml of carbodiimide (Calbiochem-Behring) for 1 hour on a rocker platform at room temperature. The dishes were then washed three times with Hanks' balanced salt solution (GIBCO) and stored empty at $-20°$ until use.

C. Selection, Screening and Production of Ascites Fluid

After cell fusion, cells were cultured in HAT medium (DMEM with 4.5 g/liter glucose containing 20% [v/v]fetal calf serum [Dutchland Laboratories, Denver, Pa.]; 13.6 μ/ml hypoxanthine [Calbiochem-Behring]; 18/μg/ml sodium methotrexate [Calbiochem-Behring]; 3.87μ/ml thymidine [Calbiochem-Behring; 0.225 μg/ml glycine [ICN Nutritional Biochemicals, Cleveland, Ohio]; 0.15 mg/ml oxaloacetate [Sigma Chemical Co., St. Louis, Mo.]; 0.05 mg/ml pyruvate [Sigma]; 0.2 U/ml bovine insulin [Sigma]; 0.8mM glutamine Flow Laboratories, McLean, Va.]; 50 IU/ml penicillin Flow]; and 50μg/ml streptomycin [Flow]at 37° C. with 5% $CO_2$ in a humid atmosphere. Seven to 10 days after the fusion, the cells were switched to HT medium (HAT medium with only 10% [v/v]fetal calf serum and no sodium methotrexate) for further culture and cloning. About 2 to 3 weeks after the fusion, 100 μl of supernatant from cultures containing hybridomas was removed and screened for Candida-specific antibodies.

Cell culture supernatants were screened for specific antibodies by an enzyme-linked immunosorbent assay (ELISA). The assay was performed by coating 96-well tissue culture plates (Costar, No. 3596) with 50/μl of a 1 μg/ml solution of the partially purified Candida proteins in 0.015 M carbonate buffer, pH 9.6, overnight at 4° C. The plates were blocked with 200 μl of a 3% (w/v) soluton of bovine serum albumin in 0.015 M carbonate buffer, pH 9.6, overnight at 4° C. Fifty μl of culture supernatants were added to the antigen-coated wells and incubated overnight at 4° C. or 3 hours at 37° C. The supernatants were tapped out and the plates were rinsed four times with 0.05 M phosphate buffer, pH 7.4, containing 0.8% (w/v) NaCl and 0.05% (w/v) Tween 20 (PBST). Fifty μl of a 1 μg/ml solution of horseradish peroxidase-labeled antimouse IgG+IgM (H+L chains) (Kirkegaard and Perry Laboratories, Gaithersburg, Md.) was added to each well and incubated 3 hours at 37° C. The second antibody was tapped out and the plates were washed as described above. One hundred μl of substrate (0.2 mM 2,2'-azino-di(3-ethylbenzthiasoline sulfonate) (Sigma) in 0.1 M citrate buffer, pH 4.0, containing 0.02% $H_2O_2$) was added to each well and allowed to react for 30 minutes at room temperature. Antibody-containing wells were visualy identified.

Positive hybrids were expanded, retested for antibody production, and subcloned twice by limiting dilution. Ascites fluid was prepared in pristane (2,6,10,14-tetramethylpentadecane; Aldrich Chemical Co., Milwaukee, Wis.) (500 μl)-primed BALB/c mice by intraperitoneal injection of $10^7$ hybridoma cells. Ascites fluid and serum was collected, clarified by centrifugation at 800×g, and stored at $-80°$ C. Immunoglobulin G (IgG) was prepared from culture supernatants by precipitation with half-saturated ammonium sulfate, pH 7.0, followed by dialysis against 0.04 M phosphate buffer, pH 6.8. The ascites, serum and concetrated culture supernatants were studied to characterize their reactivity as described in Example II. The subjects, monoclonal antibodies A2C7 and C2C7, were demonstrated by standard techniques (immunodiffusion with class-specific antisera, Litton Bionetics, Kensington, Md.) both to be of the IgG heavy chain and kappa light chain class.

The subject hybridoma cell lines were deposited in the American Type Culture Collection, Rockville, Maryland on November 1, 1983. The subject cell lines have been accorded designations ATCC #HB-8397 and ATCC #HB-8398, respectively.

EXAMPLE II

Characterization of Reactivity of Monoclonal Antibodies A2C7 and C2C7 Reactivity A. Staphylococcus aureus protein A (Staph A) immunoprecipitation (i) Iodination procedure Iodination of the partially purified proteins (proteins which eluted at 0.028 to 0.066 M NaCl in 0.05 M Tris-HCl, pH 7.8, with 0.02% (w/v) NaN3 from the DEAE column as described in Example I, section A) from *C. albicans* was performed using the Iodogen technique (Fraker and Speck, Biochem. Biophys. Res. Commun. 80:849–857, 1978). Ten μg of Iodogen (1,3,4,6-tetrachloro-3α, 6α-diphenylglycuril; Pierce Chemical Co., Rockford, Ill.), dissolved in 200 μl chloroform, was evaporated onto the surface of a clean glass (flat-bottom) vial. The Candida proteins (200μg in 200 μl of 0.1 M phosphate buffer, pH 7.4) and 1 mCi Na $^{125}$I in 0.1 N NaOH (New England Nuclear, Boston, Mass.) were added to the vial and incubated with periodic swirling at room temperature for 1 hour. The labeled proteins were separated from the unreacted iodide by gel filtration through a G-25 Sephadex (Pharmacia) column (10×200 mm). Gelatin phosphate buffer (0.1 M phosphate buffer, pH 7.4, containing 0.2% [w/v]gelatin and 0.02% [w/v]NaN3) was used as the equilibration and running buffer. The excluded peak (labeled proteins) was pooled and stored as aliquots at −80° C.

(ii) Immunoprecipitation

Immunoprecipitation was performed essentially as described by Kessler (J.Immunol. 115:1617–1624, 1975). The washing buffer was RIPA (0.01 M Tris-HCl, pH 7.4, 0.5 M NaCl, 0.001 M ethylenediaminetetraacetic acid (EDTA), 1.0% [w/v]Triton X-100, 1.0% [w/v]sodium desoxycholate, 0.1% [w/v]sodium dodecyl sulfate [SDS], and 0.02% [w/v]NaN3). The labeled antigen extract was precleared by adding it to the pellet from 8 ml of a 10% (w/v) suspension of heat-killed, formalinized S. aureus Cowan I (SAC) (Pansorbin, Calbiochem-Behring). The antigen and the SAC were incubated on ice for 1 hour with periodic vortexing and the bacteria were removed by centrifugation. Labeled antigen (precleared, $1-5 \times 10^6$ trichloroacetic acid-precipitable counts per minute) was then added to 100/$\mu$l ammonium sulfate-concentrated monoclonal supernatant, 10/$\mu$l of serum from a hybridoma-bearing mouse, or 10 $\mu$l of ascites fluid from a hybridoma-bearing mouse, and incubated 18 hours at 4° C.

Five $\mu$l of a second antibody (rabbit anti-mouse IgG, IgM, and IgA; Calbiochem-Behring) was added to each tube and incubated for 18 hours at 4° C. Excess SAC (500 $\mu$l) was added and incubated for an additional 2 hours at 4° C. The bacteria were collected by centrifugation and washed three times with RIPA buffer. The pellet was then resuspended in 2X electrophoresis sample buffer and prepared for SDS-polyacrylamide gel electrophoresis (SDS-PAGE) as described by Laemmli (Nature [USA]227:680–685, 1970). The bacteria were removed by centrifugation and the supernatant was applied to SDS 12% (w/v) polyacrylamide gels. Following electrophoresis of the immunoprecipitates, the gels were fixed and stained with Coomassie Blue (0.3% [w/v]Coomassie Blue G250 in 10% [v/v]methanol, 10% [v/v]glacial acetic acid and 80% [v/v]distilled water) for 45 minutes, destained in the above solvent without dye, dried on filter paper and exposed to Kodak AR-5 film (Eastman Kodak Co., Rochester, N.Y.) with or without DuPont Cronex Hi-Plus intensifying screens (DuPont Instruments-ACA, Wilmington, Del.). Data from this experiment are presented in FIG. 2.

EXAMPLE III

Comparison of Monoclonal Antibody Reactivity With The Reactivity of Antibodies in the Sera of Patients with Candidiasis The reactivity of monoclonal antibodies A2C7 and C2C7 was compared to the reactivity of antibodies in the sera of patients with candidiasis by Staph A immunoprecipitation. The labeled antigen and the immunoprecipitation procedures for the human sera were performed essentially as described in Example II. The differences in the procedures were that 5 $\mu$l of h0man sera were incubated with $1 \times 10^6$ trichloroacetic acid-precipitable counts per minute of the $^{125}$I-labeled antigen and that the anti-mouse second antibody was omitted. Fifty-one human sera were analyzed. The sera were divided into four groups as follows:

1. Deep tissue or disseminated candidiasis

These sera were from patients diagnosed as having deep tissue or disseminated candidiasis. The criteria for this diagnosis included (i) repeated isolation (more than one separated by 24 hours) of Candida spp. from blood; (ii) isolation of Candida spp. from normally sterile body fluids (excluding urine) or asceptically obtained deep tissue material; (iii) histological evidence of deep tissue invasion not in communication with a non-sterile surface; or (iv) endophthalmitis with typical candidal ophthalmoscopic findings and a clinical condition consistent with Candida sepsis. Included in this group were two sera from patients with locally invasive candidiasis and two sera from a patient with endocarditis due to C. parapsilosis. (Twenty-five sera were in group 1).

2. Non-invasive candidiasis

These were from patients at risk of acquiring, but apparently without, disseminated candidiasis when the sera were drawn. Patients in this group had surgery, burns, wounds, or cancer as the predisposing underlying condition. Candida spp. were isolated from mucosal surfaces and urine of many of these patients. (Ten sera were in group 2.)

3. Other fungal infections

These sera were from patients with fungal infections due to Histoplasma capsulatum, Cryptococcus neoformans, Coccidioides immitis and Aspergillus spp. (Ten sera were in group 3).

4. Normal, healthy individuals

These sera were from healthy, non-hospitalized men and women. (Six were in group 4). FIG. 3 shows autoradiographs of immunoprecipitates fractionated by SDS-PAGE. The immunoprecipitated bands migrating with an apparent molecular weight of 48–52 Kd were excised and $125_I$ was counted in a gamma counter. The results of this analysis are presented in FIG. 4.

EXAMPLE IV

Purification of 48–52 Kd Antgen to Apparaent Biochemical Homogeneity and Production of Monospecific Polyclonal Antibody A. The preparation of the mycelial cytoplasmic extract (MCE) is described in Example I B. Fractionation of the Mycelial-Phase Cytoplasmic Extract Affinity chromatography. The MCE (42 to 114 mg protein) was passed over a concanavalin A affinity column as in Example 1-A. The unbound material, e.g., mannan-depleted components, was collected (2-ml fractions) and the optical density at 280 nm was monitored spectrophotometrically (Bausch and Lomb, Rochester, N.Y.). The mannan-depleted material was pooled, dialyzed against a lyophilizable buffer of pH between about pH 7 and about pH 8, and lyophilized. The preferred lyophilizable buffer is 0.001M (NH4)HCO3, pH 7.4. Approximately 60% of the protein loaded on the concanavalin A column was recovered in the unbound fractions and was tested for the presence of mannan by crossed immunoaffinoelectrophoresis in the presence of Con A. If the unbound material contained detectable mannan, the sample was repassed over a clean Con A 4B column. The column was regenerated by eluting the bound mannans with 0.05 M alpha-methyl mannoside (Aldrich) in buffer A followed by several volumes of buffer A alone.

The mannan-depleted cytoplasmic extract (MD-CE) 152 mg/protein was put through a carboxymethyl cellulose ("CM") ion exchange column equilibrated with a buffer having buffering capacity around pH 6.5 at about 0.05M buffer ion concentration. Preferred is 0.05 M imidazole, pH 6.5. Other useful anionic buffers include acetate, barbiturate, citrate, glycine phosphate, etc. A CM-Sepharose column is the preferred carboxymethyl cellulose column. Non-binding material was washed off the column with imidazole buffer and a 0–0.3 M NaCl gradient was used to elute the binding proteins. Other salts of sodium or potassium may be used. The non-binding material and the first peak off the NaCl gradient were concentrated by Amicon filtration and then separated on 12% SDS-PAGE. After SDS-PAGE separation, the gels were washed with distilled water and stained with ice cold 0.25 M KCl/1 mM dithiothreitol (DTT) until the bands became opaque. The bands of relevant molecular weight was cut out and placed in a teflon tube where it was rinsed and destained twice and then incubated in ice-cold 1 mM DTT for 20 minutes. Five ml of elution buffer (5mM DTT, 0.15 mM NaCl, 0.1 mM EDTA, 0.05 M Tris-HCl and 0.1% SDS and PMSF 1mM) was added to the tube and a pestle was used to crush the gel. The protein was allowed to elute with gentle agitation for 2 hours at room temperature and then placed at 4° C. overnight. The material was centrifuged at 5000 rpm for 15 minutes at −2° C. to separate both acrylamide and the precipitated SDS from the isolated protein. SDS-PAGE analysis was done to check protein purity. FIG. 5 shows an example of a SDS-PAGE gel run on the proteins which were eluted from the preparative gels and subsequently used for rabbit inoculation. The gels are stained with Coomassie Blue G250. The molecular weight standards are run in the right-hand lane, and the lane on the left contains the purified 48–52 Kd protein.

C. Antibody production

New Zealand white rabbits (5Kg) were used to produce antibodies to the 48–52 Kd protein. Initial subcutaneous injections of 200–300/μg protein in incomplete Freund's adjuvant were followed by 150 μg protein in incomplete Freund's adjuvant every 2 weeks for 3 months and then once a month. The rabbits were bled weekly and antibody levels measured by rocket immunoelectrophoresis.

Staph A immunoprecipitation analysis of the polyclonal antibodies

Staph A immunoprecipitation was done on pulse labeled L-[$^{14}$C]leucine lysates (PLL) of a 37° C. hyphal high-speed supernatant preparation of C. albicans (Ahrens et al., J. Gen. Microbiol. 129:1133–1139, 1983). Two hundred μl of the PLL was precleared by incubating with 100 μl of normal IgG for 15 minutes at 37° C. Five hudred μl of Staph A was added to the mixture incubated for 15 minutes at 37° C. and 60 minutes at 4° C. After centrifugation the supernatant was decanted and added to 300 μl of Staph A and 1 mM phenylmethylsulphonyl fluoride (PMSF) and incubated for 15 minutes at 37° C. and 60 minutes at 4° C. This material was centrifuged and total disintegrations per minute determined by counting in an Intertechnique 3000 SL liquid scintillation counter. Immunoglobulins used for analysis were from rabbits inoculated with the 48–52 Kd protein.

Four mg of immunoglobulin was added to 50 μl of the precleared PLL and incubated for 15 minutes at 37° C. and 12 hours at 4° C. Five hundred μl. Staph A and PMSF was added, the material was then spun, the supernatants were counted and the pellets washed in buffer. The pellets were resuspended in electrophoresis buffer and prepared for SDS-PAGE as described by Laemmli (Nature [USA]227:680–685, 1970). The bacteria were removed by centrifugation and the supernatant applied to SDS 12% (w/v) polyacrylamide gels. Following electrophoresis of the immune precipitates, the gels were fixed and stained with Coomassie Blue (0.3% [w/v]Coomassie Blue G250 in 10% [v/v]methanol, 10% [v/v]glacial acetic acid, and 80% [v/v]distilled water) for 45 minutes, destained in the above solvent without dye, dried on filter paper and exposed to Kodak AR-5 film (Eastman Kodak Co., Rochester, N.Y.) with or without DuPont Cronex Hi-Plus intensifying screens (DuPont Instruments-ACA, Wilmington, Del.). Data from this experiment are presented in FIG. 6.

EXAMPLE V

Peptide Mapping of the Antigens Recognized by Monoclonal Antibodies A2C7 and C2C7, by Polyclonal Antibody to the 48–52 Kd Protein, and by Antibodies in Sera from Two Patients with Candidiasis Limited proteolytic digestion of the $^{125}$I-labeled protein antigens identified by immunoprecipitation was performed essentially as described by Cleveland et al. (J. Biol. Chem. 252:1102–1106, 1977). Bands were cut out of the dried gel, using a scalpel blade and rehydrated overnight in a solution of 7% (v/v) glacial acetic acid in distilled water. The digestion procedure for proteins in gel slices was followed using 0.15 μg (0.10 U of enzyme activity) of S. aureus V8 protease (Miles Laboratories, Elkhart, Inc.). The substrates ($^{125}$I-labeled proteins) and enzyme were incubated 45 minutes at the interface of the stacking and separating gel. The peptide fragmemts were separated by SDS-PAGE as described by Laemmli (Nature 227: 680–685, 1970), using 15% (w/v) acrylamide gels. The gels were fixed, stained, dried on filter paper, and exposed to Kodak AR-5 film, using DuPont Cronex Hi-Plus intensifying screens as described in Example III. Data from these analyses are presented in FIG. 7.

BRIEF DESCRIPTION OF THE DATA

FIG. 1 shows the fractions eluted from the DEAE-Sephacel column with running buffer containing 0.02–0.06 M NaCl as analyzed by SDS-PAGE. Proteins in these fractions were used to immunize mice for hybridoma production. The gel was stained by the silver technique.

FIG. 2 shows autoradiographs of the $^{125}$I-labeled antigens which were recognized by monoclonal antibodies A2C7 and C2C7, using Staph A immunoprecipitation. The partially purified Candida antigen was labeled with $^{125}$I by the Iodogen technique. Lanes 1a and 1b represent $2.5 \times 10^5$ and $5 \times 10^5$ trichloroacetic acid-precipitable counts per minute, respectively, of the 125I-labeled region A proteins which were used as the antigen in the immunoprecipitation. Lanes 2 through 12 represent the antigens which were precipitated by the rabbit, human, and monoclonal antibodies. Lanes 2a and 2b represent a 70-hour and 24-hours exposure, respectively, of the antigens recognized by the immune rabbit serum. Lane 3 shows the antigens precipitated by normal rabbit serum. Lane 4 shows the antigens precipitated by serum (#618) from a patient with endocarditis due to *C. parapsilosis*. Lanes 5a and 5b represent 70-hour and 24-hour exposure, respectively, of the antigens recognized by serum (C-21) from a patient with invasive candidiasis, and lane 6 represents serum from a normal, healthy individual. Lanes 7 and 8 represent antigens precipitated by the malignant ascites from mice inoculated with hybridomas A2C7 and C2C7, respectively. Lanes 9 and 10 represent the antigens precipitated by the malignant ascites from a mouse inoculated with another hybridoma secreting a monoclonal antibody against *C. albicans* (IgG1/kappa) and the culture supernatant from a hybridoma secreting a monoclonal antibody of non-defined specificity, respectively. Lanes 11 and 12 represent the proteins precipitated by *S. aureus* cells incubated with antigen and second antibody (rabbit anti-mouse) and *S. aureus* cells incubated with antigen alone, respectively.

FIG. 3 shows autoradiographs from Staph A immunoprecipitation of the partially purified Candida proteins from the DEAE column by antibodies in human sera. The Candida proteins were labeled by the Iodogen technique. Representative autoradiographs from sera in each group are shown. Group 1 contains sera from patients with disseminated candidiasis; Group 2 contains sera from patients with non-invasive, superficial candidiasis; Group 3 ontains sera from patients with other fungal infections; and Group 4 contains sera from healthy, non-hospitalized men and women. Panel A represents autoradiographs exposed 18.5 to 23 hours. Panel B represents a 67-hour exposure of the sera from Group 1 in panel A. Panel C is a 21-hour exposure of the antigen precipitated by *S. aureus* cells alone and the $^{125}$I-labeled Candida proteins.

Figure 4:
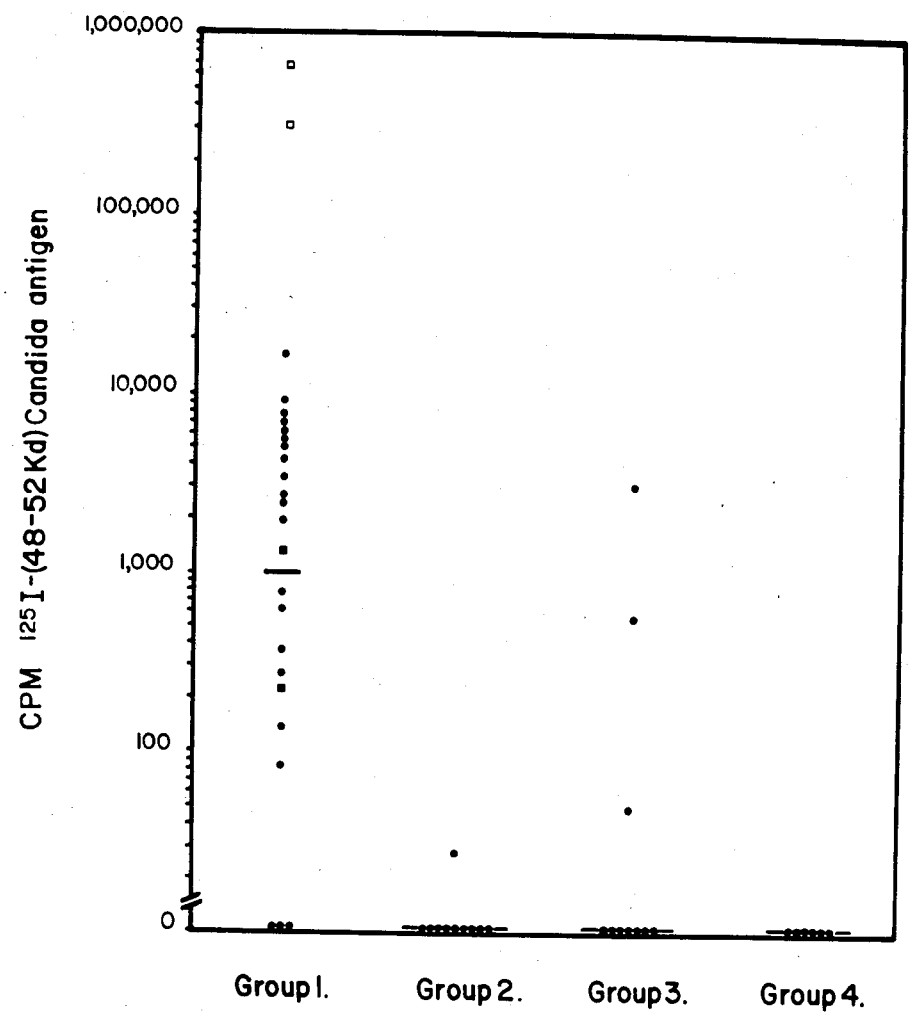

FIG. 4 shows *S. aureus* immunoprecipitation of the 48 to 52 Kd antigen of *C. albicans* by antibodies in human sera. The antigen was labeled with $^{125}$I by the Iodogen technique. The data were obtained by cutting out the 48 to 52 Kd antigen from a SDS-PAGE gel and counting it in a gamma counter. Each point represents the specific counts precipitated of the 48 to 52 Kd antigen, i.e., sample counts per minute (cpm) minus *S. aureus* cells alone cpm. Group 1 contains 25 sera from patients with disseminated or invasive candidiasis. ■ represents the sera from the two patients with locally candidiasis and □ represents the sera from a patient with endocarditis due to *C. parapsilosis*. Group 2 contains 10 sera from patients at risk of candidiasis. These patients had non-invasive, superficial candidiasis. Group 3 contains 10 sera from patients with other fungal infections. Group 4 contains 6 sera from healthy, non-hospitalized men and women. The geometric mean and standard error of the mean are as follows: Group 1 =1,000.24 (212.90 to 4,699.45) cpm; Group 2 =1.97 (1.07 to 3.63) cpm; Group 3 =6.22 (1.96 to 19.73) cpm; and Group 4 =0 (0) cpm. The F value, obtained using a one-way analysis of variance with fixed effects, is 20.27, which is highly significant at $p>0.001$.

FIG. 5 shows SDS-PAGE analysis of the 48 Kd protein eluted from preparative gels and used for rabbit inoculation. The lane on the left shows the 48 Kd protein and the lane on right shows the molecular weight standards.

FIG. 6 shows a 4-week autoradiograph of Staph A immunoprecipitation of serum from a rabbit immunized against the 48 Kd protein. All lanes contain 7000 disintegrations per minute per well. Lanes 1 and 2 represent 7000 disintegrations per minute of the $^{14}$C-leucine pulse labeled, highspeed supernatant extract. Lane 3 represents the molecular weight standards. Lanes 4 and 5 represent antigens precipitated by serum from the rabbit immunized with the 48 Kd protein.

FIG. 7 shows limited proteolysis of the three antigens (the 48 to 52 Kd protein, the 120 to 135 Kd protein, and the 35 to 38 Kd protein) immunoprecipitated by A2C7, C2C7, two human sera, and serum from a rabbit immunized against the 48–52 Kd Candida protein. The three antigens immunoprecipitated by each sera were cut out of the original gel and treated with *S. aureus* protease. The fragments generated by the enzymatic digestion were separated on 15% acrylamide SDS-gels. The patterns of the major peptide fragments are shown. The lanes and their contents are: 1, the 48 to 52 Kd antigen precipitated by *S. aureus* cells alone; 2, the 48 to 52 Kd antigen precipitated by serum (C-21) from a patient with invasive candidiasis; 3, the 48 to 52 Kd antigen precipitated by serum from the immune rabbit; 4, the 48 to 52 Kd antigen precipitated by serum (#618) from a patient with endocarditis due to *C. parapsilosis;* 5, the 48 to 52 Kd antigen precipitated by C2C7; 6, the 48 to 52 Kd antigen precipitated by A2C7; 7, the 120 to 135 Kd antigen precipitated by #618; 8, the 120 to 135 Kd antigen precipitated by C2C7; 9, the 120 to 135 Kd antigen precipitated by C-21; 10, the 120 to 135 Kd antigen precipitated by serum from the immune rabbit; 11, the 120 to 135 Kd antigen precipitated by A2C7; 12, the 35 to 38 Kd antigen precipitated by A2C7; 13, the 35 to 38 Kd antigen precipitated by serum from the immune rabbit; 14, the upper band of a doublet that was precipitated by #618 in the molecular weight range of 35 to 38 Kd; 15, the lower band of a doublet that was precipitated by #618 in the molecular weight range of 35 to 38 Kd; 16 the 35 to 38 Kd antigen precipitated by C-21; and 17, the 35 to 38 Kd antigen precipitated by C2C7. Lanes 1 and 2 represent a 400-hour exposure; lanes 3a through 6a represent a 22.5-hour exposure; lanes 3b through 6b represent a 7-hour exposure; lanes 7 and 8 represent a 400-hour exposure; lanes 9 through 11 represent a 215-hour exposure; lanes 12 and 13a through 16a represent a 215-hour exposure; and lanes 13b through 16b and 17 represent a 91-hour exposure. All exposures were done in the presence of intensifying screens.

Staph A immunoprecipitation was performed to characterize the apparent molecular weight(s) of the antigen(s) which were recognized by monoclonal antibodies A2C7 and C2C7. The data in FIG. 2 demonstrate that monoclonal antibodies A2C7 and C2C7 oth immunoprecipitate a minimum of three proteins with the apparent molecular weights of 120–135 Kd, 48–52 Kd, and 35–38 Kd as determined by SDS-PAGE on 12% (w/v) acrylamide gels (see Example 11 for a description of the methos). The 48–52 Kd protein recognized by these monoclonal antibodies is a major protein in the partially purified extract of *C. albicans* as seen from the silver-stained gel of the fractions comprising the extract (see FIG. 1).

The relationship of the three antigens recognized by monoclonal antibodies A2C7 and C2C7 was studied by limited proteolysis using *S. aureus* v8 protease. The data from this analysis are presented in FIG. 7. Limited proteolytic digestion of the three antigenic proteins (the 120–135 Kd, the 48–52 Kd, and the 35–38 Kd proteins) shows that three proteins share a significant amount of primary structure. The data also demonstrate that A2C7 and C2C7 both recognize the same subset of Candida proteins. The shared primary structure between these three proteins may define the antigenic determinant recognized by the two monoclonal antibodies. It is likely that other Candida proteins which have the same or similar primary structure will be recognized by monoclonal antibodies A2C7 and C2C7.

The serodiagnostic potential of these monoclonal antibodies was studied by characterizing the antibodies in sera from patients with candidiasis by Staph A immunoprecipitation (Example III). The data from this study is presented in FIGS. 3 and 4. The data presented in FIG. 4 demonstrate that patients with invasive forms of candidiasis have significantly higher levels ($p < 0.001$ using a one-way analysis of variance with fixed effects) of antibodies against a 48–52 Kd Candida protein than do patients with non-invasive forms of candidiasis, patients with other fungal infections or normal, healthy individuals. Antigens of the same apparent molecular weights that were immunoprecipitated by antibodies in the sera of two patients with invasive candidiasis, were studied by limited proteolysis as described in Example IV. These data (FIG. 7) demonstrate that the antigens recognized by the antibodies in the two sera of patients with invasive candidiasis are the same antigens recognized by monoclonal antibodies A2C7 and C2C7. These data establish that the monoclonal antibodies recognize a serodiagnostically important antigen (48–52 Kd) from *C. albicans*. It is likely that this antigen can be detected in extract of other Candida species, as sera from a patient with endocarditis due to *C. parapsilosis* recognizes the 48–52 Kd antigen from *C. albicans*.

A 48–52 Kd protein was purified to apparent homogeneity (FIG. 5) and was used to immunize a rabbit. The specificity of the resulting monospecific, polyclonal antisera was examined by immunoprecipitation of $^{14}C$-labeled cytoplasmic proteins. As shown in FIG. 6, a single band of 48–52 Kd was immunoprecipitated. As shown by limited proteolysis, this $48^{52}$ Kd protein was the same one precipitated by the monoclonal antibodies and the sera of humans with disseminated candidiasis (FIG. 7). This antiserum also precipitated $^{125}I$-labeled proteins of region A with molecular weights of 120–135 Kd and 35–38 Kd which, as described above, have very similar peptide maps to the 48–52 Kd protein.

The monoclonal and polyclonal antibodies of the present invention have diagnostic application recognizing Candida antigens. These antibodies are believed useful in detecting antigen in body fluids in immunosuppressed patients using a variety of standard assays including, but not limited to, latex agglutination, radio immunoassay (RIA), enzyme-linked immunosorbent assay (ELISA), or other suitable antigen detection systems. The body fluid of the patient is contacted with antibody, and the material bound thereto is measured.

The Candida antigens whose purification is taught herein also have diagnostic utility. We have shown in retrospective studies (Strockbine, Largen, Zweibel and Buckley, *Inf. & Imm.*, accepted) that antibodies in the sera of patients with disseminated Candidiasis recognize these antigens, whereas antibodies in the sera of (1) normal individuals (2) patients with colonized by Candida, but not having invasive disease, and (3) patients with other fungal infections do not recognize these antigens. Detection systems such as ELISA, RIA, latex agglutination, immunoblot assay, or other suitable assay systems can be used for the detection of antibodies against the described antigens.

Although only two hybridomas, each producing a single monoclonal antibody against cytoplasmic antigens of *C. albicans* antigen is described, it is contemplated that the present invention encompasses all monoclonal antibodies exhibiting the characteristics described herein.

Further included within the subject invention are methods for preparing the monoclonal antibodies described above employing the hybridoma technique illustrated herein. Although only two examples of hybridomas are given herein, it is contemplated that one skilled in the art could follow the immunization, fusion, and selection methods provided herein and obtain other hyhridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, it is contemplated that all hybridomas producing antibody having th reactivity characteristics described above are included within the subject invention, as are methods for making this antibody employing the hybridoma.

The partial purification of immunogen used in the production of monoclonal antibodies according to the present invention is illustrated by the partial purification of cytoplasmic antigens of *C. albicans*. However, it is believed that this novel procedure has application for the partial purification of cytoplasmic antigens of other pathogenic Candida species.

The procedure for preparing essentially biochemically pure immunogen used in the production of monoclonal and monospecific, polyclonal antibodies according to the present invention is illustrated for the 48–52 Kd cytoplasmic antigen species of *C. albicans*. However, it is believed that this purification procedure for isolating cytoplasmic antigens has application to other pathogenic Candida species.

The present invention may be embodied in other specific forms without departing from the spirit or essential attributes thereof and, accordingly, reference should be made to the appended claims, rather than to the foregoing specification, as indicating the scope of the invention.

What is claimed is:

1. A diagnostic method for disseminated or invasive candidiasis comprising:
   a. contacting blood serum with a composition containing a substantially bichemically pure preparation of a cytoplasmic antigen of *C. albicans*, said antigen having an apparent molecular weight selected from the group consisting of 48–52 Kd, 35–38 Kd and 120–135 Kd, said antigen being detectable in humans during disseminated candidiasis but not during non-invasive *C. albicans* infections; and
   b. detecting antibody bound by the antigen of said preparation.

2. A diagnostic method according to claim 1 wherein the detecting means is selected from the group consisting of latex agglutination, radioimmunoassay, enzyme-linked immunosorbent assay, and immunoblot assay.

3. A diagnostic method according to claim 1 wherein the antigen is the 48–52 Kd antigen.

4. A diagnostic method according to claim 1 wherein the antigen is recognized by monoclonal antibody produced by a hybridoma selected from the group of hybridomas consisting of ATCC #HB-8397 and ATCC #HB-8398.

5. A substantially biochemically pure preparation of a cytoplasmic antigen of *C. albicans*, said antigen having an apparent molecular weight selected from the group consisting of 48–52 Kd, 35–38 Kd and 120–135 Kd, said antigen being detectable in humans during disseminated candidiasis but not during non-invansive *C. albicans l infections.*

6. A preparation according to claim 5 of the 48–52 Kd antigen.

7. A substantially biochemically pure preparation of a cytoplasmic antigen of *C. albicans* which is recognized by a monoclonal antibody produced by a hybridoma selected from the group of hybridomas consisting of ATCC #HB-8397 and ATCC #HB-8398.

* * * * *